United States Patent [19]

Wang

[11] Patent Number: 5,320,110
[45] Date of Patent: Jun. 14, 1994

[54] PLEURAL BIOPSY SYRINGE-NEEDLES

[76] Inventor: Ko P. Wang, 11006 Nacirema La., Stevenson, Md. 21153

[21] Appl. No.: 40,086

[22] Filed: Mar. 30, 1993

Related U.S. Application Data

[63] Continuation of Ser. No. 783,991, Oct. 29, 1991, abandoned.

[51] Int. Cl.$^5$ ............................................. A61B 10/00
[52] U.S. Cl. ................................... 128/753; 128/754; 128/765
[58] Field of Search ............... 128/749, 750, 751, 752, 128/753, 754, 763, 765, 766, 771, 760, 762; 606/167, 170, 171; 604/272, 274

[56] References Cited

U.S. PATENT DOCUMENTS

| | | | |
|---|---|---|---|
| 2,590,895 | 4/1952 | Scarpellino | 604/272 |
| 2,748,769 | 6/1956 | Huber | 604/272 |
| 3,844,272 | 10/1974 | Banko | 128/753 |
| 3,929,123 | 12/1975 | Jamshidi | 128/754 |
| 4,266,555 | 5/1981 | Jamshidi | 128/753 |
| 4,441,509 | 4/1984 | Kotsifas et al. | 128/757 |
| 4,603,694 | 8/1986 | Wheeler | 128/312 |
| 4,619,272 | 10/1986 | Zambelli | 128/753 |
| 4,702,260 | 10/1987 | Wang | 128/753 |
| 4,817,631 | 4/1989 | Schnepp-Pesch et al. | 128/753 |
| 4,832,044 | 5/1989 | Gorg | 128/753 |
| 4,967,762 | 11/1990 | DeVries | 128/753 |
| 4,986,278 | 1/1991 | Ravid et al. | 128/753 |
| 4,986,827 | 1/1991 | Akkas et al. | 606/107 |

OTHER PUBLICATIONS

Becton, Dickinson and Company Brochure "Biopsy Needles..." Oct. 1974.

Primary Examiner—Stephen C. Pellegrino
Assistant Examiner—Guy V. Tucker
Attorney, Agent, or Firm—Cushman, Darby & Cushman

[57] ABSTRACT

Pleural biopsy device for reducing the probability of effecting pneumothorax in a patient during a pleural biopsy procedure, for facilitating the cutting of sample tissues of the parietal pleura, and for aspirating and removing large quantities of fluid from the patient's body without switching needles. Proximal ends of two hollow, inner and outer needles are directly attached to the plunger and the barrel of a syringe, respectively. When properly assembled, the syringe, and the inner and the outer needles form a closed system that seals out the external air and the arrangement permits tissue collection without intermediate needle withdrawal during the procedure.

11 Claims, 12 Drawing Sheets

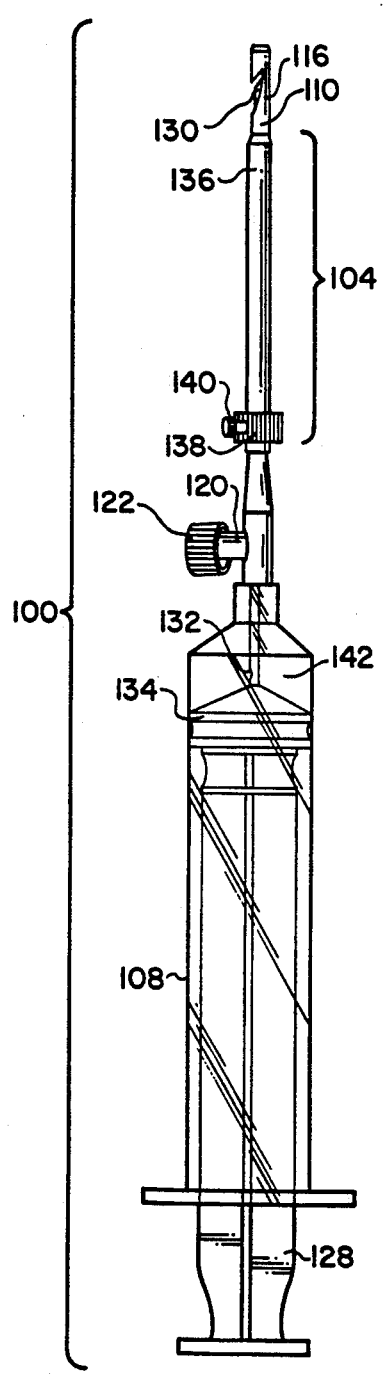
FIG. 7
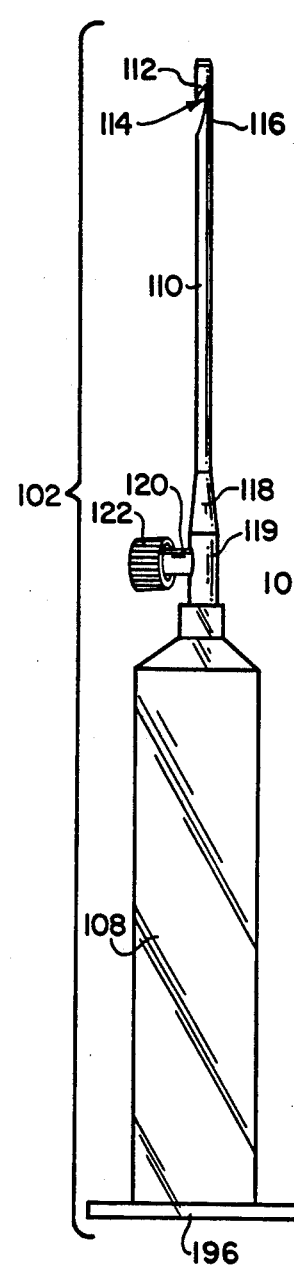
FIG. 8
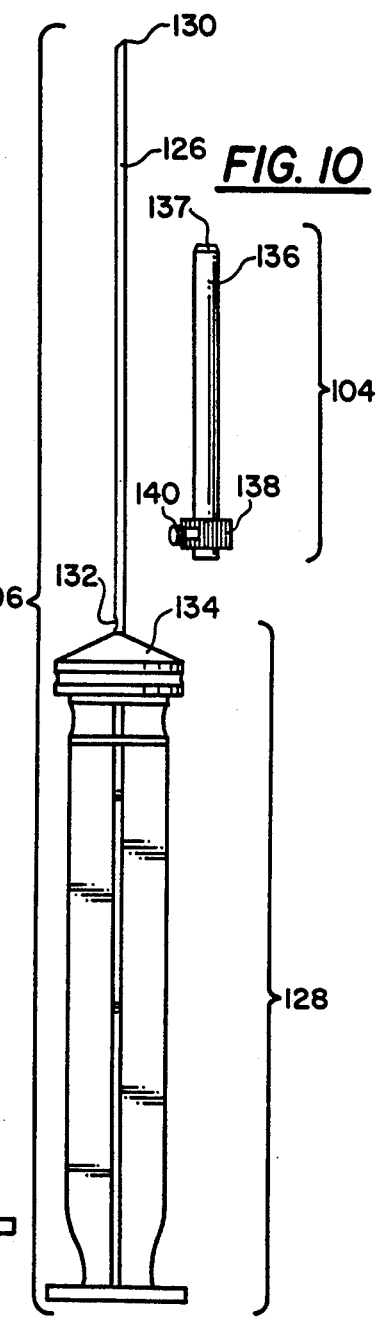
FIG. 9
FIG. 10

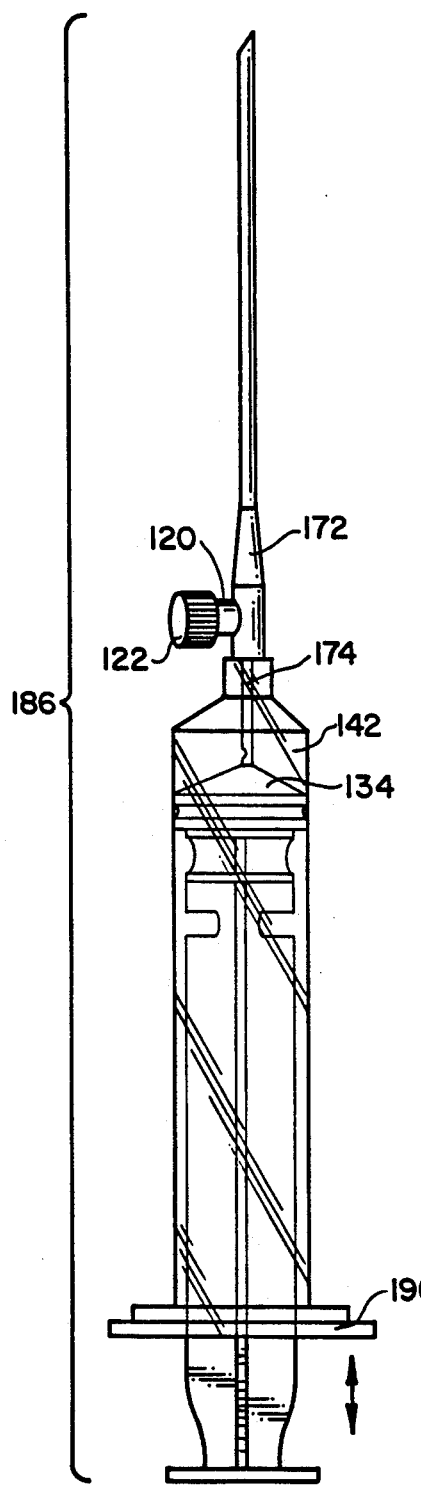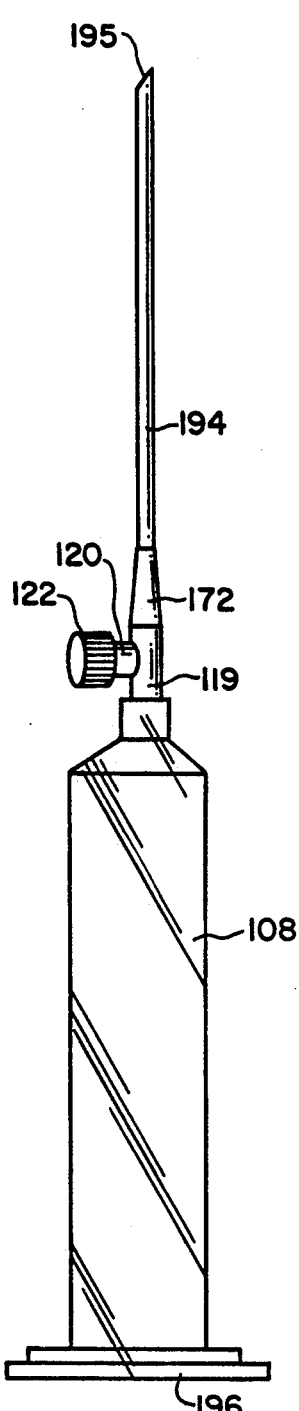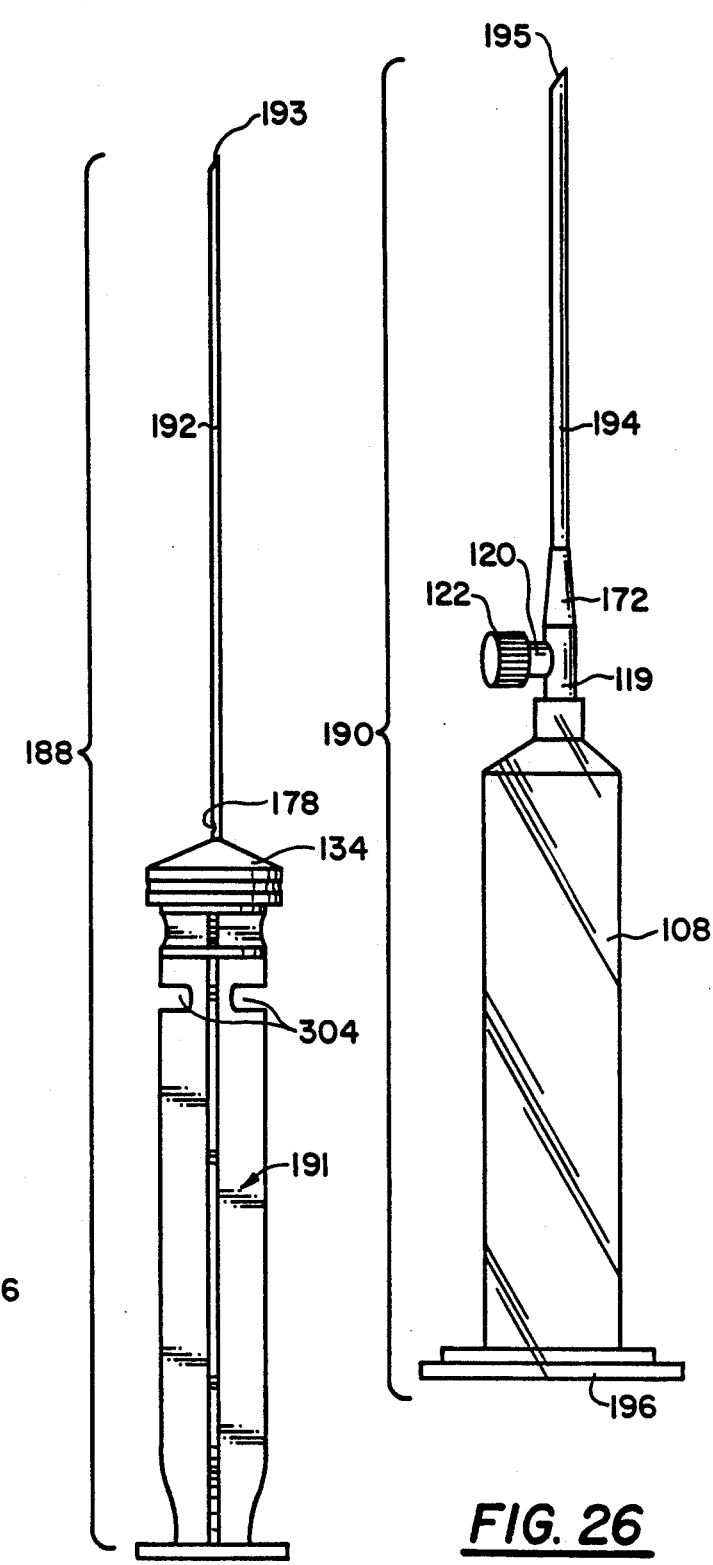
FIG. 24
FIG. 25
FIG. 26

PLEURAL BIOPSY SYRINGE-NEEDLES

This is a continuation of application No. 07/783,991, filed on Oct. 29, 1991, which was abandoned upon the filing hereof.

BACKGROUND OF THE INVENTION

1. Field of the Invention

The present invention relates to improved pleural biopsy procedure needles. Such needles are used for obtaining tissue samples of the parietal pleura for biopsy examination purposes and to more easily permitting thoracentesis procedures.

2. Description of Related Art

Two types of needles are and have been widely used for a number of years for obtaining pleural biopsy specimens. One of these is commonly denominated a Cope needle which is comprised of a number of structural pieces collectively shown at 20, in FIG. 1. The Cope biopsy device consists of four parts: an outer cannula 22, a hooked biopsy trocar 24, an interior hollow trocar 26, and a solid innermost obturator or stylet 28. To obtain a pleural biopsy specimen using the Cope needle, stylet 28 is inserted inside hollow trocar 26, which, in turn, is placed inside outer cannula 22. At this point, biopsy trocar 24 is not yet part of the assembled combination. An incision is made in the patient and the assembly of pieces 22, 26 and 28 is then introduced into that incision. Because the distal end of stylet 28 and trocar 26 are both beveled and sharpened, the needle assembly can be pushed through tissue until the distal end lies within the pleural cavity of a patient. Next, stylet 28 is removed from within trocar 26. When this step occurs an opening may be allowed into the pleural cavity. Thereafter, a syringe is removably attached to the proximal end of hollow trocar 26. Connection of a syringe could not occur prior to this as stylet 28 had to be removed. Aspiration of fluid into the newly attached syringe indicates the correct placement or location of the distal end of the assembly consisting of cannula 22 and trocar 26 inside pleural cavity. After aspiration, hollow trocar 26, together with its syringe, is withdrawn and replaced with the hooked biopsy trocar 24, which is also removably connected to a syringe. It may be noted that, during the withdrawal and replacement procedures used on stylet 28, trocar 26 and biopsy trocar 24, the possible opening created by the removal of hollow trocar 26 into the pleural cavity, as noted above, needs to be occluded in order to avoid a leakage of air into pleural cavity. Such leakage can cause pneumothorax, precipitating a respiratory failure.

Following insertion of hooked trocar 24, another aspiration step may be employed to again check for proper positioning of the distal end of trocar 24. The whole assembly, cannula 22 and trocar 24, is rotated about its longitudinal axis until a direction guard 30 on the proximal end of hooked trocar 24 indicates the inferior position of distal hook 32. This position is essentially as shown in FIG. 2. Next, the whole assembly is pulled backwards. Resistance against pulling signifies that hook 32 of trocar 24 has been caught by tissue of the pleura. While hook 32 remains engaged with the pleura tissues, outer cannula 22 is advanced to cut off the hooked piece of pleura tissue. This is shown in FIG. 3. Thereafter, removal of the whole assembly, cannula 22 and trocar 24, along with the severed sample of tissue between the outer cannula 22 and trocar 24, completes the biopsy tissue collection procedure. Only one specimen is collectable.

The other type of biopsy needle is commonly known as the Abram's needle. The Abram's needle also consists of a number of structural elements collectively shown in FIG. 3. The three pieces forming the Abram's needle are an outer trocar 36, having a blunt, closed distal end, an inner, hollow, cutting cannula 38, and an inner, solid stylet 40. Prior to use, all three pieces are assembled with stylet 40 located within cannula 38 and that combination being in turn inserted into outer trocar 36. Following an incision in the patient's chest, the Abram's needle is inserted through the incision into the patient's pleural cavity 154. Following insertion, solid stylet 40 is removed and a syringe is removably attached to the then exposed proximal end of the inner cutting cannula 38. A small quantity of fluid is thereafter aspirated to check for the correct placement of the distal end of the assembly inside pleural cavity. After aspiration, the inner cutting cannula is withdrawn to open and expose a cutting edge on a distal end notch 42 formed in outer trocar 36. Next, outer trocar 36 is pulled rearwardly to catch or engage the pleura on the distal side of notch 42, after which inner cutting cannula 38 is rotatingly advanced to cut off a piece of the engaged pleura. This cutting action is partially shown in FIG. 6. Finally, the whole needle assembly, together with the tissue sample now lodged inside the outer trocar 36 at the distal end of inner cannula 38, is withdrawn from the patient completing the procedure and with a single tissue sample.

SUMMARY OF THE INVENTION

It is an object of the present invention to provide a pleural biopsy needle assembly with improvements for reducing the probability of effecting pneumothorax in a patient during pleural biopsy tissue sampling procedures.

It is a further object of the present invention to improve upon various features for obtaining samples of parietal pleura.

It is another object of the present invention to improve features for more easily aspirating and removing varying, large or small, quantities of fluid from the patient's body without switching or interchanging needles.

According to the present invention, the proximal ends of hollow, inner and outer, components of the needle assembly are directly attached, by suitable means or by directly holding the needle elements in place, to the plunger and the barrel of a syringe, respectively. The inner hollow needle component is provided with a small aperture adjacent its proximal end and slightly distally of the rubber stopper at the end of the plunger. The proximal end of the outer hollow needle component is, in turn, connected to the distal end of the syringe barrel. The proximal end of the outer needle component could, if desired, include a larger diameter opening at the connection point to the syringe barrel. Also, the connection between the needle and syringe barrel would preferably also include a separate connector member, a T-shaped structure that would include hollow flow passage formed perpendicularly to the main axial flow path through the connector member. The perpendicular flow passage can provide an outlet to the atmosphere that includes suitable flow controlling valving so that this passage is normally closed.

During normal operation of the needle assembly, this hollow flow passage is formed with a standard exterior leur lock connection and will normally be capped with a removable cap, thereby closing the outlet.

One embodiment of the present invention includes three separate pieces: an outer cannula, a syringe plunger with an attached inner hollow trocar, and a syringe barrel with an attached hooked biopsy trocar. To use the device, the hollow trocar is inserted inside the hooked biopsy trocar, which, in turn, is placed inside the outer cannula. As was the case with prior art needles, this combination is also introduced through an incision made in the patient and pushed into the pleural cavity. At this juncture, the procedure is radically different since no needles are removed or new ones inserted. Aspiration of fluid is easily accomplished by only slightly withdrawing the plunger within the syringe barrel. This action would also slightly withdraw the attached inner hollow trocar. Fluid will flow through the inner hollow trocar, through the aperture at the proximal end thereof and then into the cavity formed inside the syringe barrel. Aspiration can be directly accomplished without changing any needles. Simultaneously, the whole assembly can be pulled slightly outwards to catch the pleura by the hooked biopsy trocar. Then the outer cannula is rotatingly advanced to cut the hooked piece of tissue.

Another embodiment of the present invention is comprised of two separate pieces: an outer trocar attached directly to the syringe barrel, that includes a notch formed adjacent the distal end and an inner cutting cannula directly attached to the syringe plunger. Aspiration of pleural fluid can again be easily done by pulling the plunger rearwardly but without withdrawing it fully from the syringe barrel. A sample of the pleura may be obtained by first pulling the whole assembly slightly backwards to catch the pleura at the notch near the distal end of the outer trocar and then advancing the inner cutting cannula to shear the hooked piece by simply pushing in the plunger.

Another embodiment of the present invention again comprises two separate pieces attached to a syringe: an outer cannula and an inner cutting cannula, respectively attached to the syringe barrel and plunger. Each of the cannulae has a notch at its distal end. Also, the outer cannula has a small hole proximal to its notch.

The whole assembly is designed for obtaining a plurality of samples of the pleura with a single penetration of the assembly into the pleural cavity. After the aspiration of pleural fluid to check for proper position, a first sample may be obtained by slightly withdrawing the inner cannula so that its tip is proximal to the notch of the outer cannula; catching the pleura at the notch of the outer cannula; and severing a piece of the pleura by pushing the inner cannula toward distal end of the outer cannula. A second piece of tissue may be obtained by first adjusting the location of the inner cannula so that its notch is exposed through the notch of the outer cannula; catching the pleura between the notch of both the inner and outer cannula; and severing a piece of the pleura by pushing the inner cannula axially toward the distal end of the outer cannula.

According to yet another embodiment of the present invention, two pieces of a needle-syringe assembly are configured for socothentesis. Its structure omits the notches but is otherwise similar to above-described embodiments, and its description is therefore omitted.

All of the above embodiments may be used with a plunger guide, which can be attached to the end of the barrel of a syringe, to prevent rotation of the plunger with respect to the barrel and thereby assume the proper or desired orientation of the inner and outer needle components to assure tissue collection.

In the present invention, for both pleural biopsy and thoracentesis procedure, because the needles and the syringe form a closed system, there is little or no probability of accidentally exposing critical parts of the patient's body to atmospheric air.

Furthermore, in one embodiment for pleural biopsy and another for thoracentesis, the tip of inner needle is tapered to avoid accidental plugging. Furthermore, the small hole at the proximal side of the notch of the outer needle allows the flow of fluid therethrough in case the inner needle does become clogged.

During aspiration of pleural fluid or during a procedure, such as thoracentesis, by opening the outlet flow passage, large quantities of fluid collected inside the syringe may be drained from a patient either by a pumping motion of the plunger with respect to the barrel, without undesirable exposure of parts of the patient's body or by attaching suction devices to the outlet. This provides a very convenient way to remove and drain fluid without any need to switch needles or syringes as the latter became filled with fluid.

Other objects, features and characteristics of the present invention, as well as the methods and operation and functions of the related elements of the structure and to the combination of parts and economies of manufacture, will become apparent upon consideration of the following description and the appended claims with references to the accompanying drawings, all of which form a part of this specification, wherein like reference numerals designate corresponding parts in the various figures.

BRIEF DESCRIPTION OF THE DRAWINGS

FIG. 7 is a side elevational view of a first embodiment of the present invention;

FIG. 8 is a side elevational view of the outer syringe section and its associated needle shown in FIG. 7;

FIG. 9 is a side elevational view of the inner syringe section and its associated needle shown in FIG. 7;

FIG. 10 is a side elevational view of the outer cannula shown in FIG. 7;

FIG. 24 is a side elevational view of a fourth embodiment of the present invention;

FIG. 25 is a side elevational view of the inner syringe section and its associated needle shown in FIG. 24;

FIG. 26 is a side elevational view of the outer syringe section and its associated needle shown in FIG. 24;

Figure 1:
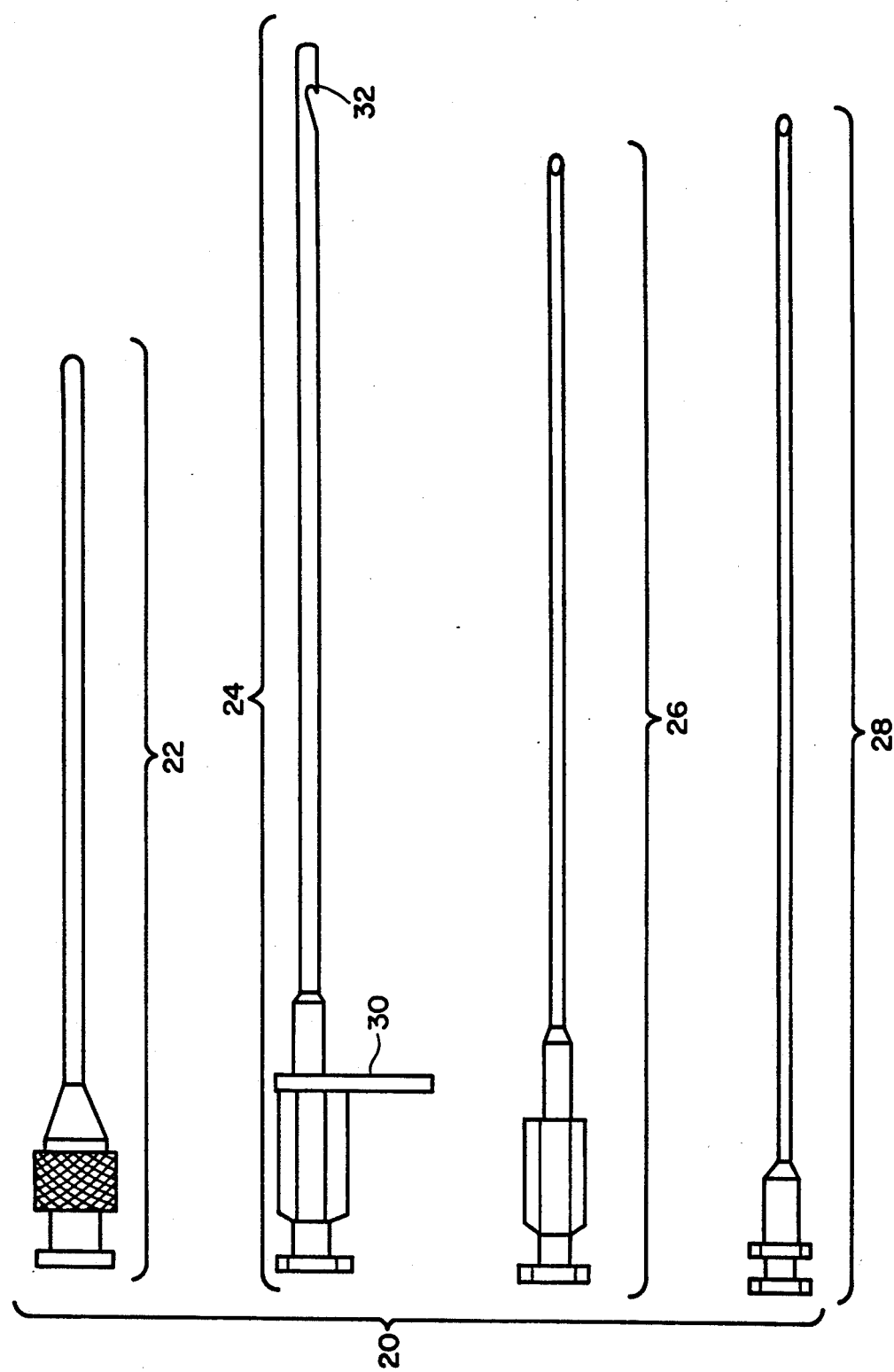
FIG. 1 is a side elevational view of the elements that together comprise the known Cope needle.
Figure 2:
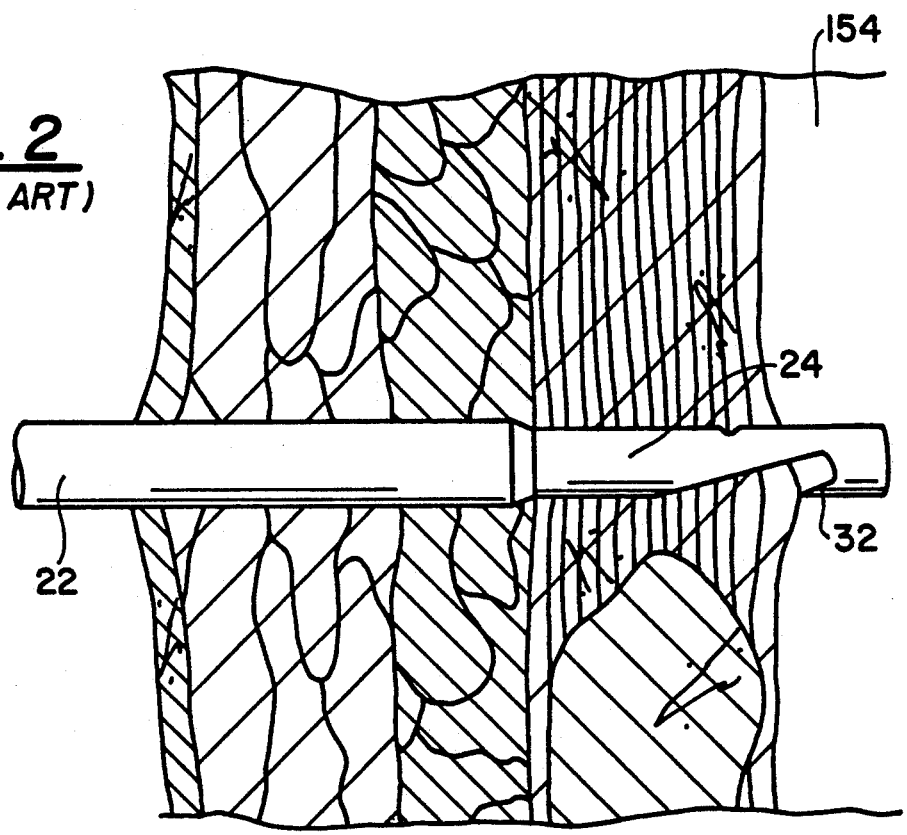
FIG. 2 shows a side elevational view of the tip of the Cope needle in contact with the parietal pleura prior to tissue sampling.
Figure 3:
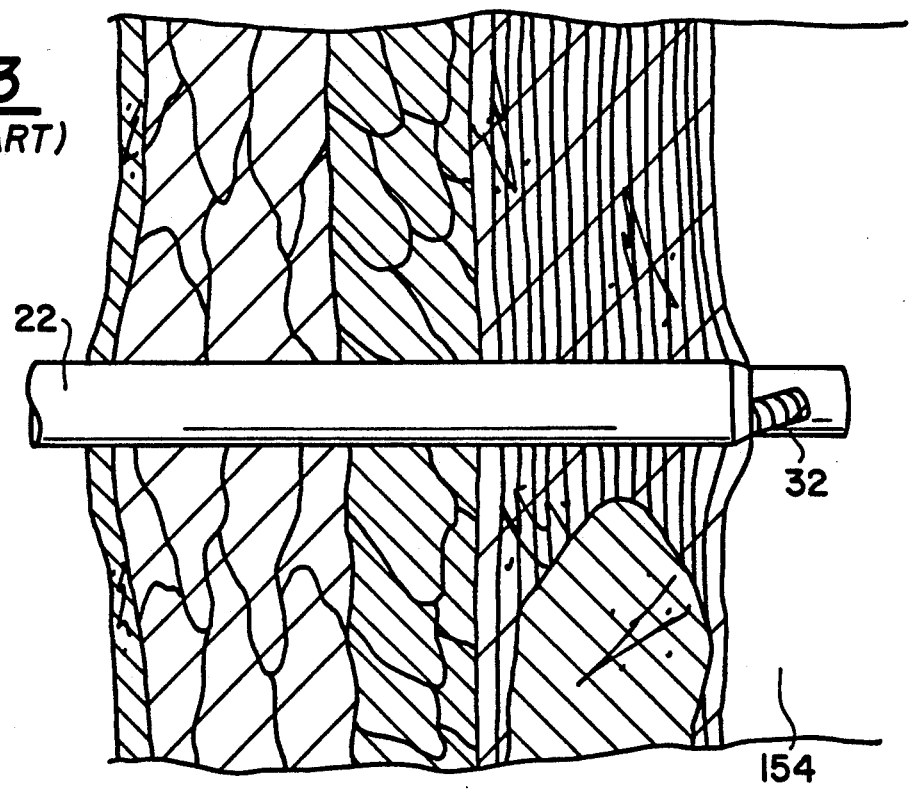
FIG. 3 shows a side elevational view of the tip of the Cope needle during tissue sampling.
Figure 4:
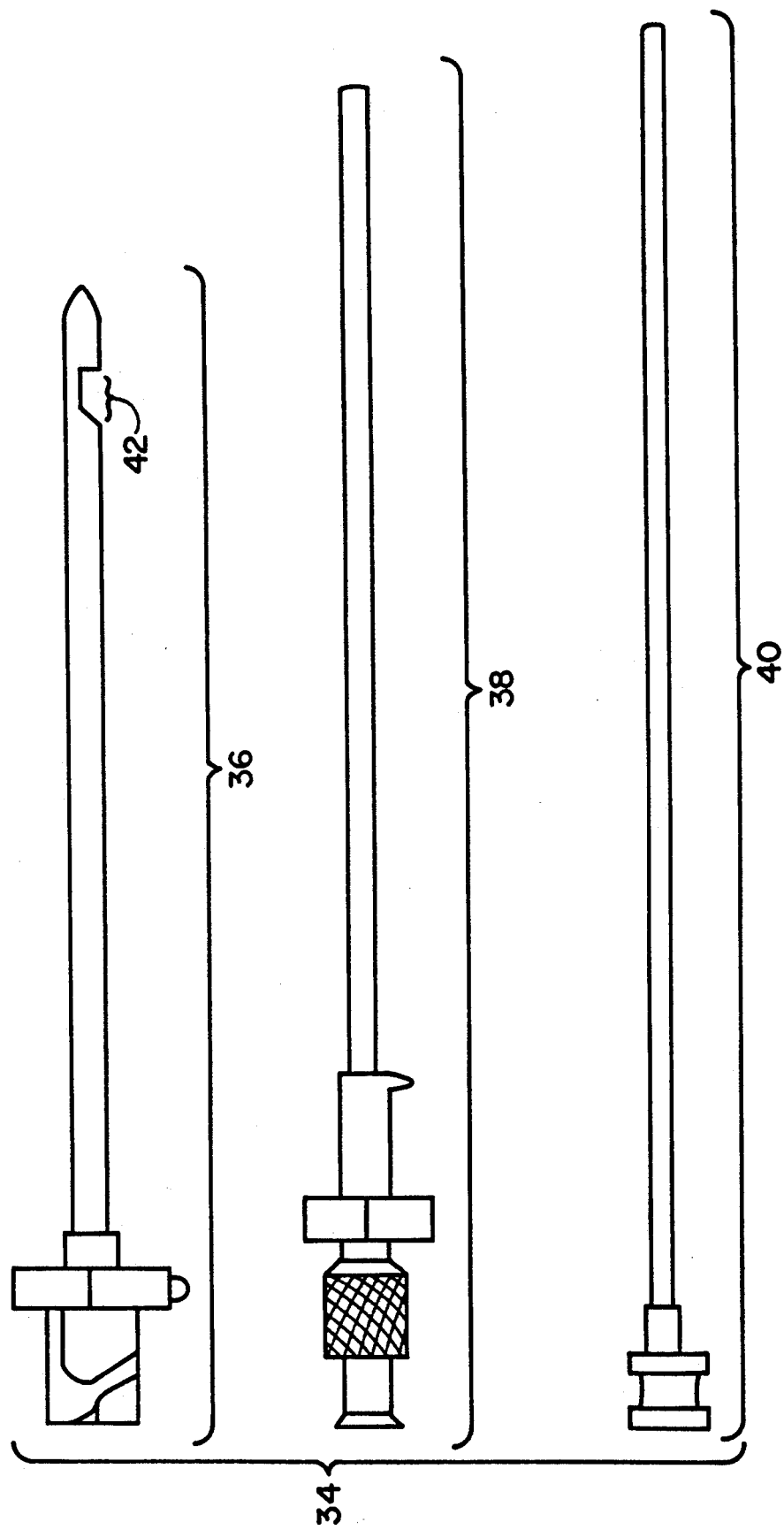
FIG. 4 is a side elevational view of the elements that together comprise the known Abram needle.
Figure 5:
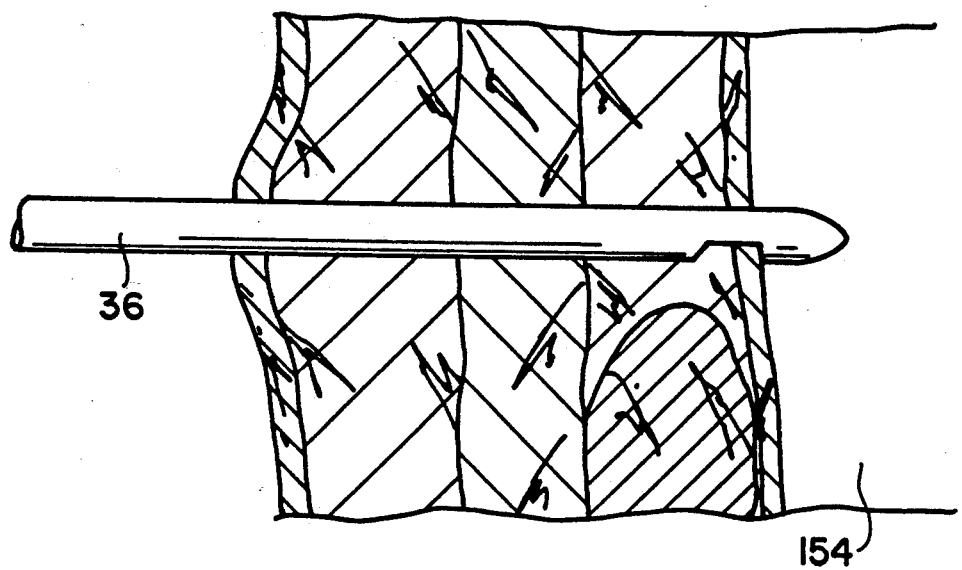
FIG. 5 shows a side elevational view of the tip of the Abram needle in contact with the parietal pleura prior to tissue sampling.
Figure 6:
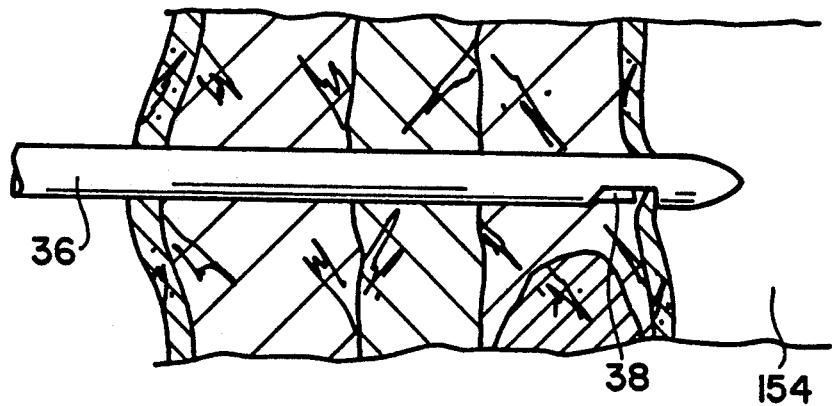
FIG. 6 shows a side elevational view of the tip of the Abram needle during needle sampling.

DETAILED DESCRIPTION OF THE EXEMPLARY PREFERRED EMBODIMENTS OF THE PRESENT INVENTION

FIGS. 7-10 show a first embodiment of the present invention which employs a hooked biopsy trocar-syringe together with an outer cannula and an inner cannula.

As shown in FIGS. 7 and 8, the assembly is generally indicated at 100 and includes a hooked biopsy trocar-syringe portion 102 that is comprised of a syringe barrel 108 and a hooked, hollow biopsy trocar 110, whose outer diameter is much smaller than that of barrel 108. Trocar 110 is secured to syringe barrel 108 by any convenient method, such as an adhesive that can be sterilized, or by having the distal end of barrel 108 molded directly onto the proximal end of trocar 110. Hooked biopsy trocar 110 is tubular and has, as its name indicates, a rearwardly facing hook 112 formed at a position spaced rearwardly from its distal end. Hook 112 is formed by cutting a notch 114 thereabout which is cut partially into the trocar sidewall. A hole 116 is formed on the opposite side of the trocar from notch 114 to allow any fluid that might become blocked by tissue being collected to escape and thus relieve pressure. Notch 114 is about 5 mm in length and is spaced about 10 mm from the distal end of trocar 110. Hole 116 has about a 1 mm diameter and can be spaced about 10 mm from the distal end and preferably on the side wall opposite the rear half portion of notch 114.

The inner and outer diameters of hooked biopsy trocar 110 are about 4 mm and 4.5 mm and has an overall length of about 10 cm.

Alternatively, the proximal end of trocar 110 can be secured in a needle support 118, formed, for example, from adhesive, or molded directly to the proximal end of trocar 110, which in turn can be secured to the distal end of a T-shaped connector 119. The proximal end of connector 119 can be secured, by suitable adhesive, or molded directly to the distal end of syringe barrel 108. The T-connector 119 includes a right- angle outlet 120 with the exterior or outlet end including a standard leur lock fitting over which a cap 122 can be removably secured.

Another portion of the assembly 100, as shown in FIG. 9, is hollow trocar-syringe portion 106 comprised of a hollow trocar 126 and a syringe plunger 128. Trocar 126 has a tapered tip 130 and a hollow interior passage that extends from tip 130 to its proximal end and to a 0.5 mm diameter hole 132, positioned slightly distally forward of a rubber seal 134 provided on the distal end of plunger 128.

The overall length, the inner diameter, and the outer diameter of hollow trocar 126 are about 11 cm, 3.0 mm and 3.4 mm, respectively.

The third portion of assembly 100 is an outer cannula 104 comprised of a hollow tube 136 having a circumferentially sharpened, beveled cutting edge 137 at its distal end. A fastener 138 circumscribes the proximal end of hollow tube 136 and a screw-lock 140 is provided to lock the outer cannula 104 onto outer trocar 110.

Assembly 100 is formed by inserting the hooked biopsy trocar 110 inside outer cannula 104 and the placement of hollow trocar-syringe portion 106 inside hooked biopsy trocar-syringe portion 102. This places trocar 126 inside trocar 110 and plunger 128 inside barrel 108. Outer cannula 104 may be fixed in a proximal position on hooked biopsy trocar 110, as shown in FIG. 7, by tightening screw-lock 140.

The assembled components of assembly 100, as in FIG. 7, form a connected space comprised of the lumen of hollow trocar 126 and syringe cavity 142. Therefore, by pushing plunger 128 into barrel 108, fluid inside the syringe may be forced to travel from syringe cavity 142 initially through proximal hole 132 to and out of the tapered tip 130 via the lumen of trocar 126. Conversely, withdrawing plunger 128 within barrel 108 will pull fluid located about tip 130, through the lumen of hollow trocar 126 and into syringe cavity 142 via aperture 132.

Tip 130 of trocar 126 is tapered mainly to prevent the opening at tip 130 from becoming plugged with tissue. However, if tip 130 does become clogged with tissue or other material, during the sliding motion of outer cannula 104 to cut a sample tissue caught inside distal notch 114 (FIGS. 11 and 12), fluid trapped in the lumen of trocar 126 or near the distal tip of hooked biopsy trocar 110, wherever fluid pressure builds with plunger movement, that fluid can escape through hole 116.

Figure 28:
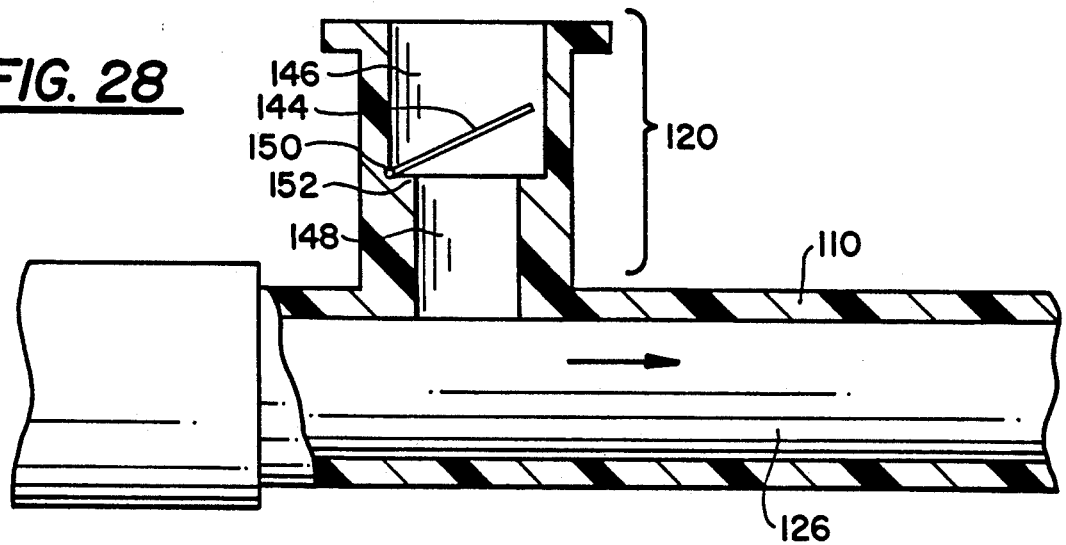
FIG. 28 is a cross-sectional side view of a flap valve and surrounding parts when the flap valve is open.
Figure 29:
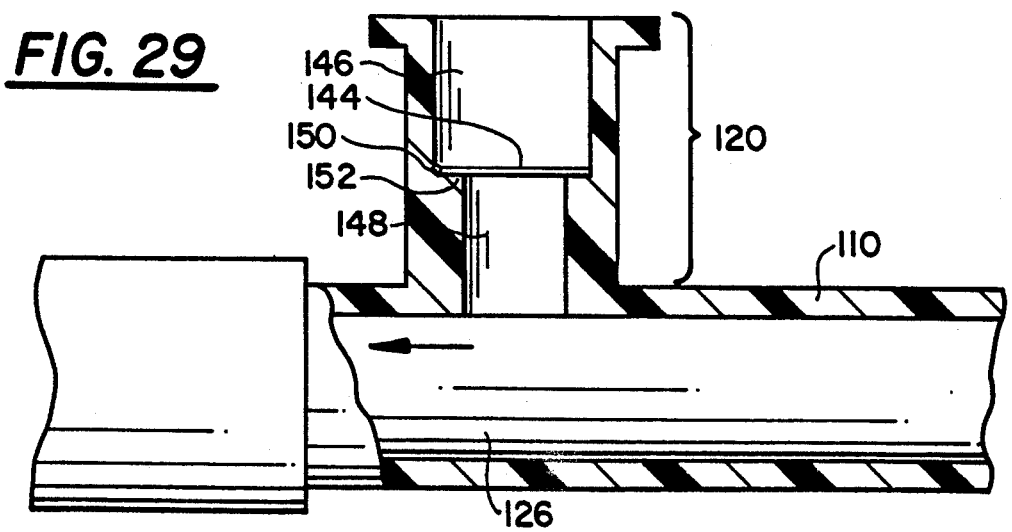
FIG. 29 is a cross-sectional side view of the flap valve and surrounding parts when the flap valve is closed.

Fluid trapped or purposely collected inside syringe cavity 142 may be drained through the T-connector 119 and specifically by un-capping outlet 120. As shown in FIGS. 28 and 29, outlet 120 preferably includes a normally closed flap valve 144 positioned between upper chamber 146 and lower chamber 148. This valve 144 is designed to allow only unidirectional flow of pleural fluid. Assuming the syringe cavity 142 is filled with pleural fluid, as it would be following the initial aspiration of pleural fluid, when plunger 128 and hollow trocar 126 traverses in a forward direction toward distal end of hooked biopsy trocar 110, the positive pressure on the fluid pushes outwardly against flap valve 144, thus opening the valve, as in FIG. 28. This pressure forces fluid passage through outlet 120. If flap valve 144 is fixed at a joint 150, which allows the rest of flap 144 to rotate about that point so that the application of positive fluid force opens flap valve 144 about that joint 150. However, when the plunger 128 and hollow trocar 126 move rearwardly toward the proximal end of assembly 100, the now negative fluid pressure on flap valve 144 will pull the flap closed; flap valve 144 catches against a ridge 152 at the interface between upper and lower chambers 146 and 148 of the outlet 120 and prevents fluid from entering the syringe cavity 142 or the lumen of hollow trocar 126 under that condition. All suction force is applied at tip 130.

The unidirectional passage of fluid through flap valve 144 allows fluid inside the syringe to be expelled over time by the forward/rearward pumping motion that can be imparted to plunger 128 with respect to barrel 108. Thus, the combination of flap valve 144 and outlet 120 allows large quantities of pleural fluid, whose source is located about tip 130 to be easily drained without switching syringes.

Alternatively, if desired, a suction device (not shown) could be connected to outlet 120 so that with tip 130 within the pleural cavity unwanted fluid could be drained in a continuous flow manner.

Figure 11:
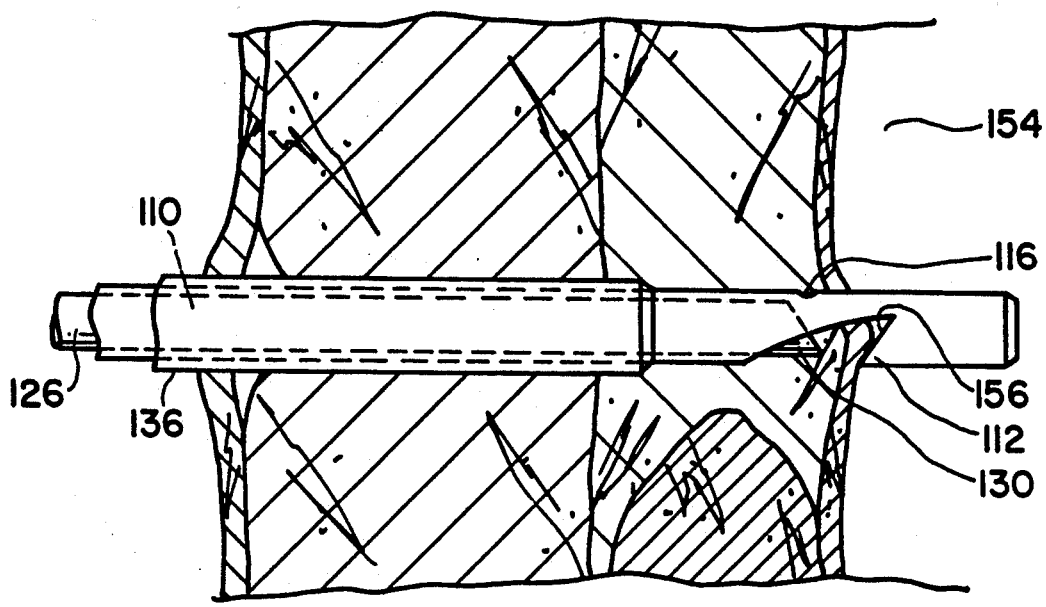
FIG. 11 is a side elevational view of the tip of the embodiment shown in FIG. 7 in contact with the parietal prior to tissue sampling.
Figure 12:
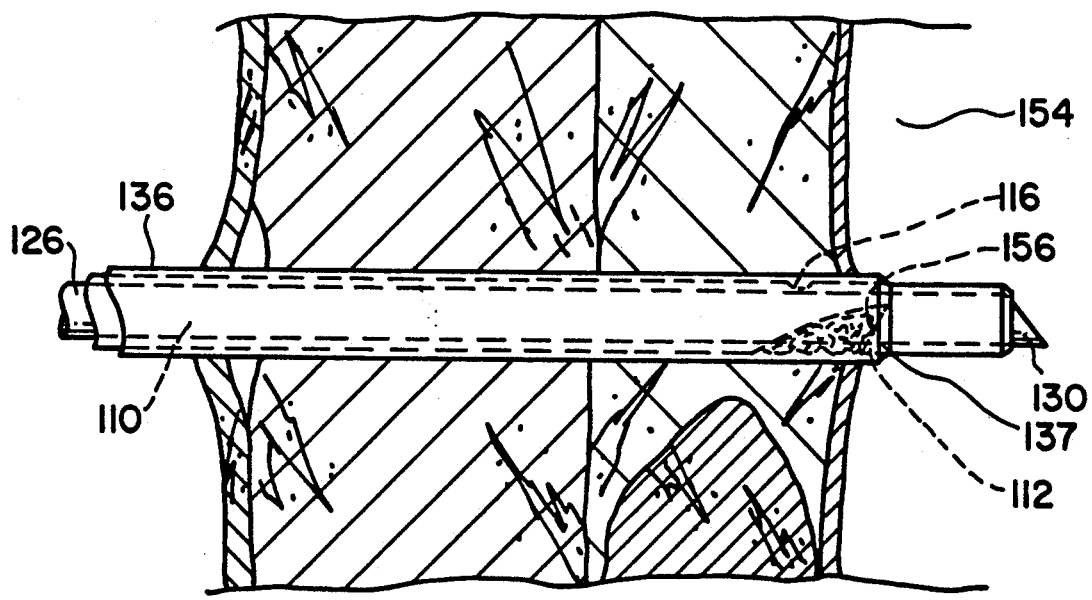
FIG. 12 is a side elevational view of the tip thereof following tissue collection.

To perform a pleural biopsy procedure using needle assembly 100, following assembly, the combination, with plunger 128 fully inserted within syringe barrel 108, is introduced through an incision in the patient's chest wall until the distal end lies within the pleural cavity 154, as in FIGS. 11 and 12. Next, plunger 128 is withdrawn slightly to aspirate pleural fluid, which travels from around tip 130 through its opening and the lumen of trocar 126 to syringe cavity 142 via aperture 132. If hooked biopsy trocar 110 is improperly placed within the patient, any attempts at aspiration will fail to collect pleural fluid; in other words, the aspiration of pleural fluid verifies the correct placement of the distal end of the biopsy device correctly in the pleural cavity. The aspiration step will fill the hollow trocar 126 with pleural fluid and automatically expose cutting edge 156 of distal notch 114 as trocar 126 is drawn rearwardly. Then, with distal notch 114 preferably in inferior position, the whole assembly 100 is moved slightly rearwardly. Resistance against such pulling indicates that hook 112 has engaged a piece of parietal pleura. Next, outer cannula 104 is advanced, with rotary motion, along trocar 110 to cut off a piece of parietal pleura that will be stored in notch 114. Leaving cannula 104 in a forward position, the removal of needle assembly 100 from the host patient completes the biopsy process.

FIGS. 13-17 show a second embodiment of the present invention generally indicated as needle assembly 160. The component parts of assembly 160 include an inner cutting cannula 174 connected to a syringe plunger 128 which together are generally referenced at 162 and shown in FIG. 15. Also included is an outer trocar 166 connected to a syringe barrel 108, collectively referenced at 164 in FIG. 14. The parts of needle assembly 160 which are identical to those of needle assembly 100 have been labelled with the same reference numerals for ease of understanding.

Figure 13:
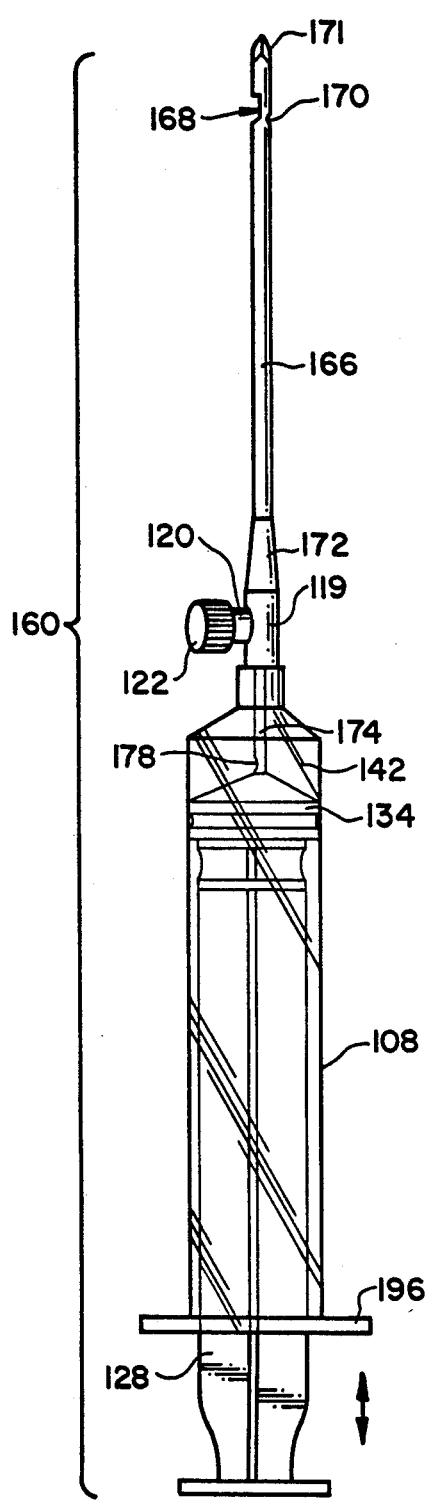
FIG. 13 is a side elevational view of a second embodiment of the present invention.
Figure 14:
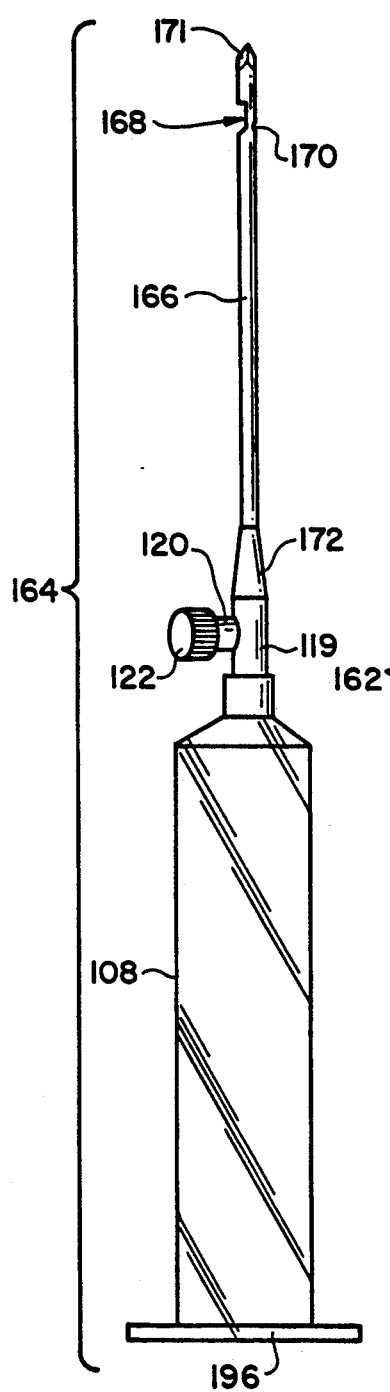
FIG. 14 is a side elevational view of the outer syringe section and its associated needle section shown in FIG. 13.
Figure 15:
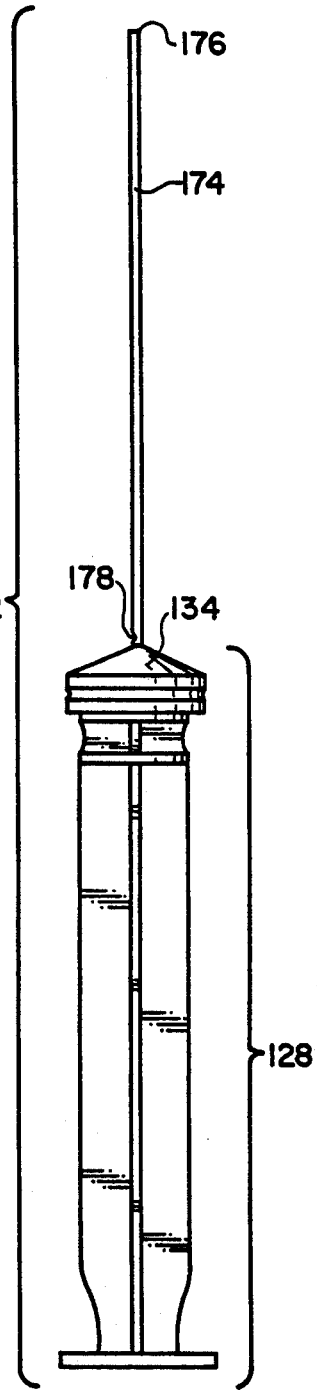
FIG. 15 is a side elevational view of the inner syringe section and its associated needle shown in FIG. 13.

As shown in FIG. 13, the outer trocar portion 164 is comprised of a syringe barrel 108 and an outer trocar 166. Outer trocar 166 is tubular with a hollow interior, and has a distally positioned notch 168 and an aperture 170 positioned to extend through the trocar side wall opposite notch 168. The exact positioning of this aperture 170 is not critical but is preferably in the proximal half of the wall opposite notch 168. In this embodiment, notch 168 begins and the aperture is located about 5 mm and 7 mm, respectively, axially rearwardly from the tip 171 of trocar 166. Tip 171 is preferably sharpened as shown in FIGS. 13, 14 with beveled surfaces. It should also be noted that notch 168 opens into the lumen within hollow trocar 166. The dimension of distal notch 168 is about 5 mm×3 mm, and the diameter of distal hole 170 is about 1 mm. Unlike notch 114 as in FIG. 8, notch 168 needle does not include a protruding hook and the functioning of notch 168 is described below. The shape and structure of needle support 172 and connector member 119 are identical to the corresponding structures described above.

The inner and outer diameters of outer trocar 166 are about 4 mm and 4.5 mm. Also, trocar 166 is about 10 cm long.

Inner cutting cannula portion 162 is comprised of a hollow, inner cutting cannula 174 which is directly connected, by any convenient method such as, for example, adhesive, or molded to syringe plunger 128. Inner cutting cannula 174 has a circumferentially sharpened distal tip 176 that is open and leads through the lumen of cannula 174 to a 1 mm diameter proximal hole 178, positioned slightly distally from the rubber seal 134 which forms part of the distal end of plunger 128. This location of hole 178 assures a fluid connection with the syringe cavity 142.

The length, the inner diameter, and the outer diameter of inner cutting cannula 174 are about 9 cm, 3.0 mm and 3.4 mm, respectively.

To use needle assembly 160, inner cannula portion 162 is inserted inside outer trocar portion 164. By pushing or pulling plunger 128 inside barrel 108, fluid may be forced to travel from syringe cavity 142 to tip 176 and not through notch 168 or from notch 168 to tip 176 and then into syringe cavity 142 via hole 178 in cannula 174.

If the open end at tip 176 of cannula 174 becomes obstructed, or if the notch 168 became obstructed, during the tissue sampling, fluid trapped near the distal tip of outer trocar 166 may escape through aperture 170.

Figure 16:
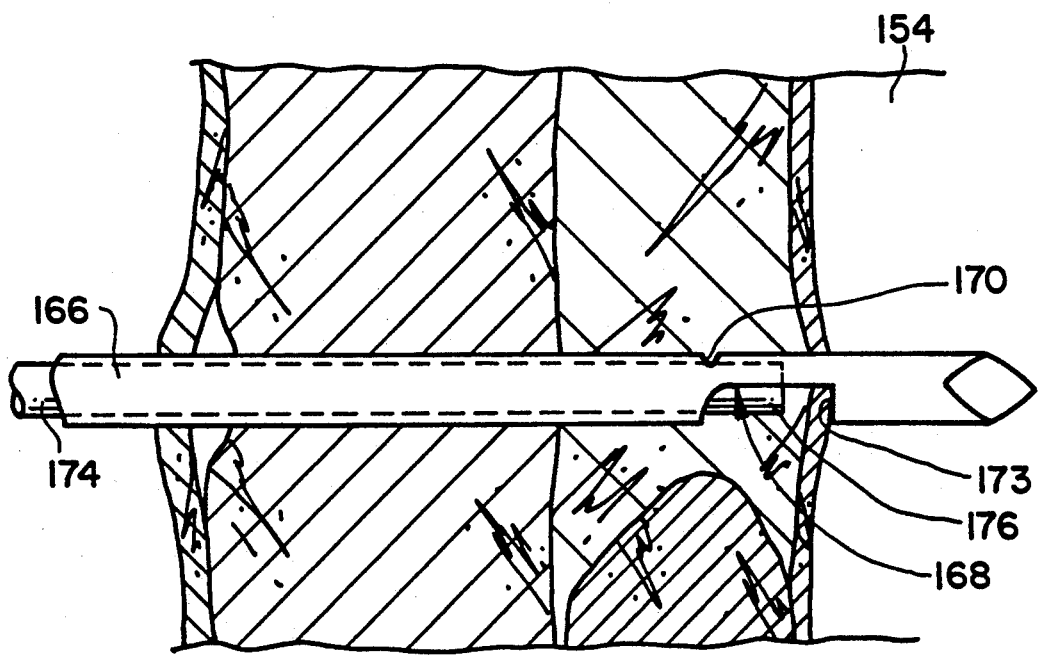
FIG. 16 is a side elevational view of the tip of the embodiment shown in FIG. 13 in contact with the pleura prior to tissue sampling.
Figure 17:
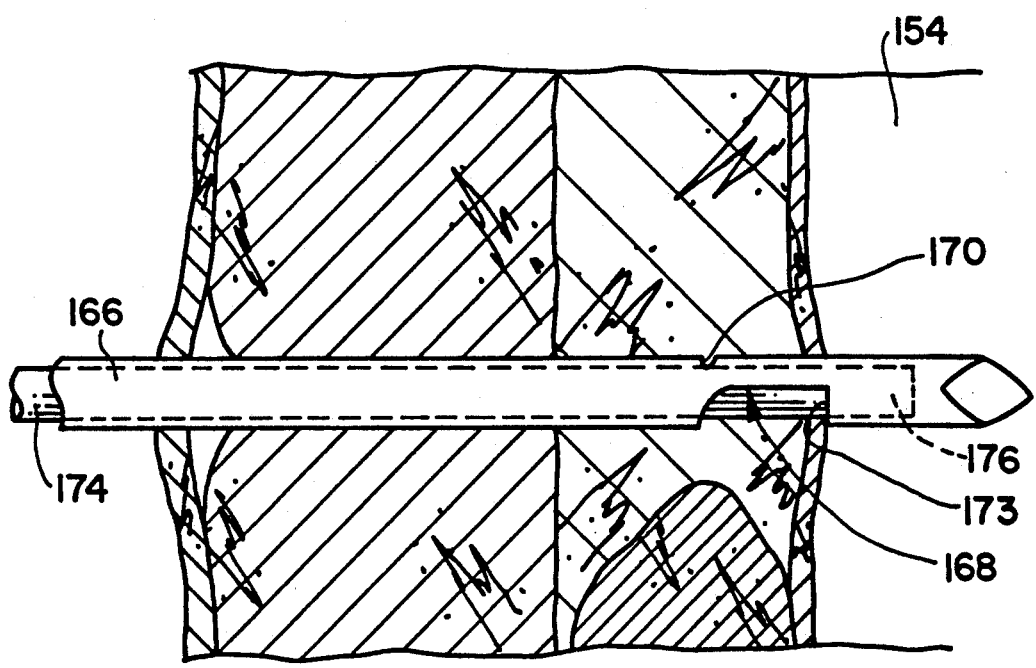
FIG. 17 is a side elevational view of the tip thereof following tissue collection.

After needle assembly 160 is connected together, the distal end is inserted through an incision in the chest wall and into the pleural cavity 154 (see FIGS. 16 and 17). Next, the syringe is used to aspirate pleural fluid. If outer trocar 166 is improperly placed within the patient, any attempts at aspiration will fail to collect pleural fluid; thus, just as in the biopsy using needle assembly 100, aspiration of pleural fluid verifies the correct placement of the needles and fills air space within the biopsy device. The aspiration process will automatically open distal notch 168 as the inner cannula 174 is moved proximally together with the rearward movement of plunger 128. Then, with distal notch 168 properly positioned, preferably in inferior position, the whole assembly 160 is pulled rearwardly. Again, resistance against the pull indicates that the distal surface or edge 173 of notch 168, as shown in FIG. 16, has engaged a piece of parietal pleura. As the inner cutting cannula 174 is advanced the tip 176 will force tissue against surface 173, thereby cutting a piece of parietal pleural. Removal of needle assembly 160 from the host patient completes the biopsy procedure.

Figure 18:
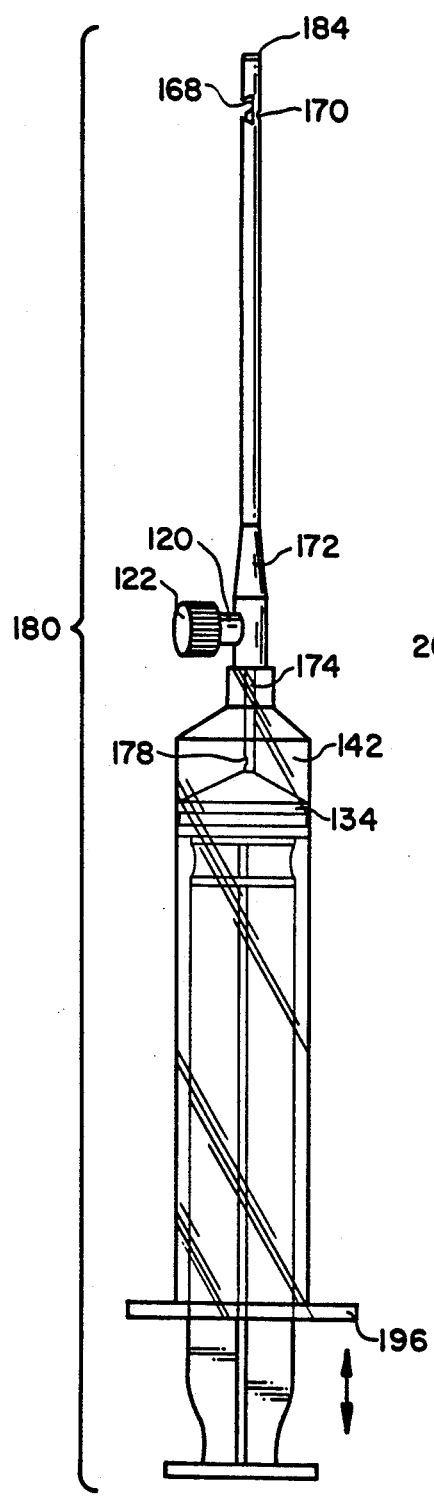
FIG. 18 is a side elevational view of a third embodiment of the present invention.
Figure 19:
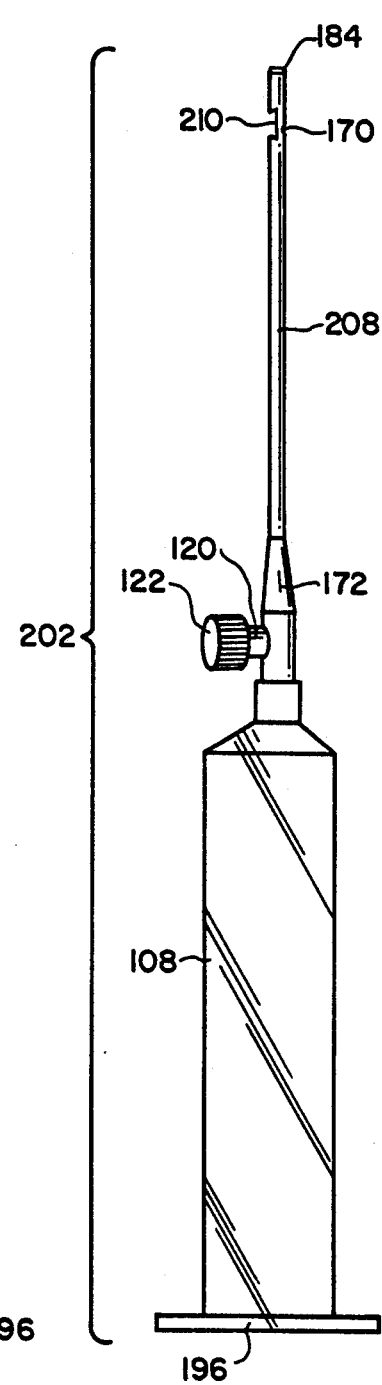
FIG. 19 is a side elevational view of the outer syringe section and its associated needle shown in FIG. 18.
Figure 20:
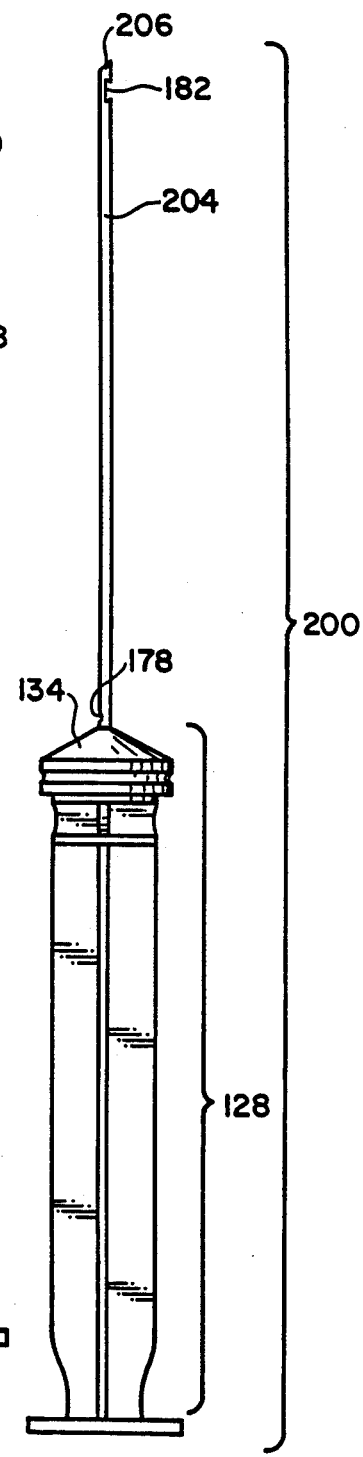
FIG. 20 is a side elevational view of the inner syringe section and its associated needle shown in FIG. 18.

A third embodiment, needle assembly 180, of the present invention also includes two main structures comprising an inner portion 200 and an outer portion 202, as shown in FIGS. 18-20. Common parts corresponding to those of needle assemblies 100 and 180 remain labelled with the same reference numerals.

As shown in FIG. 18, the structure and dimension of the needle assembly 180 are similar to needle assembly 160. Differences between two devices lie in the structure and shape of the tips of needle components in order to accomplish different objectives as explained below.

Inner portion 200, as in FIG. 20, is comprised of an inner cutting cannula 204 which is hollow and provided with a tapered tip 206. In addition, cannula 204 itself includes a distally positioned notch 182, located approximately 5 mm rearwardly from tip 206. Portion 200 also includes a plunger 128 to which the cannula 204 is suitably attached as previously described for the earlier embodiments.

Outer portion 202, as in FIG. 19, is comprised of an outer, hollow trocar 208 which also includes a sharpened distal end, tip 184 preferably in the form of a bevelled cylindrical cutting edge. The remaining portions shown in FIG. 20 have been previously described.

The inner diameter, the outer diameter, and the length of the outer trocar 208 are approximately 3.5 mm, 4 mm, and 10 cm, respectively. The corresponding dimensions for inner cutting cannula 204 are approximately 3.0 mm, 3.4 mm, and 11 cm, respectively. The lengths of cannula notch 182 and trocar notch 210 are each about 5 mm.

The procedure for using the third embodiment 180 is almost identical to that for using needle assembly 160 insofar as a first specimen is concerned. However, there is a major difference thereafter in that an additional tissue sample of pleura is obtainable without withdrawal of the whole assembly. The first sample is obtained generally as was explained above for needle assembly 160. To obtain another sample, the whole assembly must first be pulled out of the patient's body, the first sample removed from the needle, and the procedure for obtaining a sample would then be repeated. In pleural biopsy using the third embodiment 180, two tissue samples may be obtained with a single penetration of the needles into the patient's chest wall.

Figure 21:
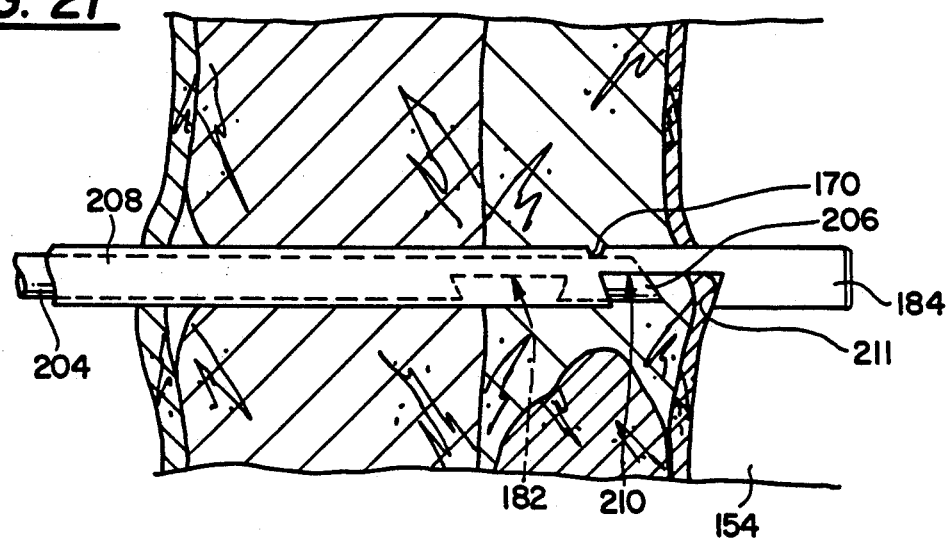
FIG. 21 is a side elevational view of the tip of the embodiment shown in FIG. 18 in contact with the parietal pleura prior tissue sampling.
Figure 22:
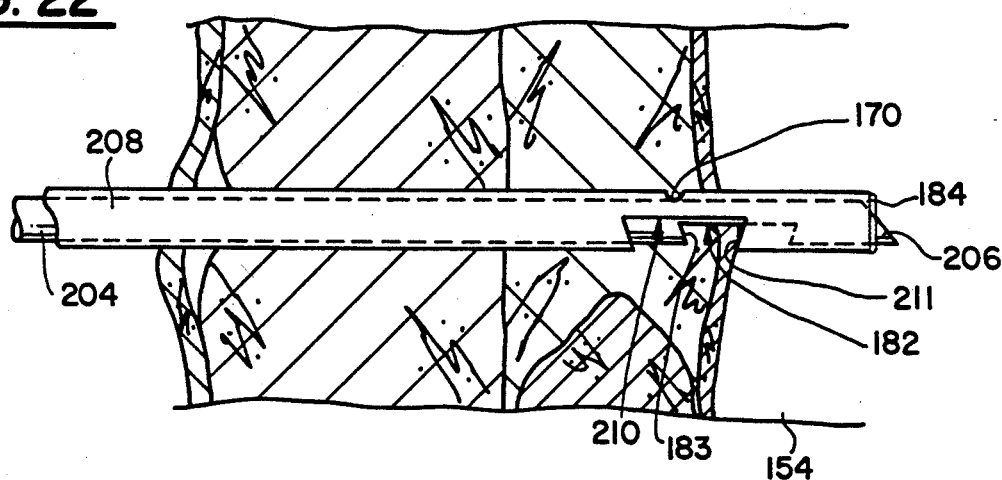
FIG. 22 shows a side elevational view of the tip of the third embodiment after a first sample has been obtained and prior to a second sampling.
Figure 23:
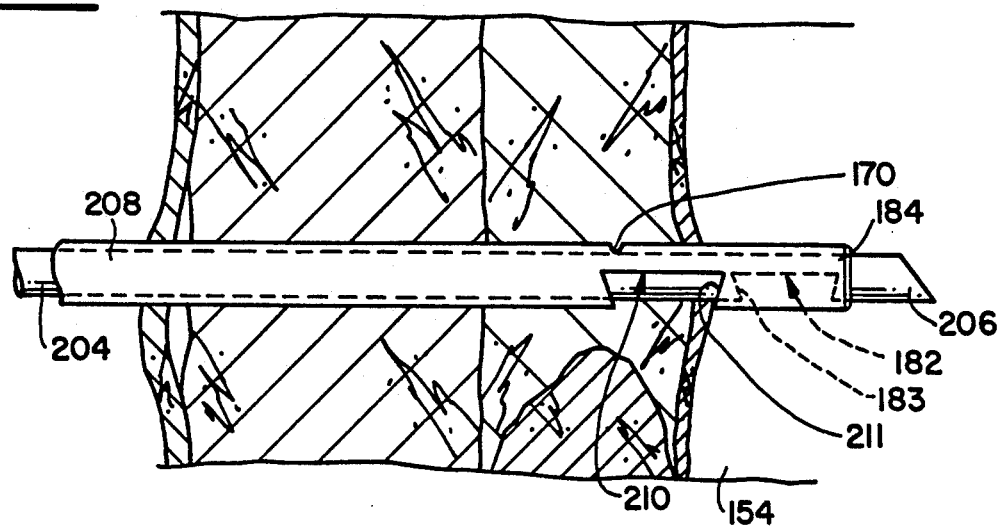
FIG. 23 shows a side elevational view of the tip of the third embodiment after a second sample has been obtained.

The procedure for obtaining two samples is as follows. After aspiration of pleural fluid, to confirm proper placement of the distal end of the assembly, the outer notch 210 is opened as inner cannula 204 slides proximally. The whole assembly 180 is then pulled slightly outwards. Resistance against pull indicates that edge portion 211 of notch 210 has engaged the pleura. At this point, the position of the distal ends of outer trocar 208 and inner cutting cannula 204 would be approximately as shown in FIG. 21. Next, by pushing inner cutting cannula 204 inwardly relative to outer trocar 208, a first sample tissue may be sheared off between tip 206 and edge portion 211. Subsequently, inner cutting cannula 204 is positioned within trocar 208 so that its notch 182 is exposed within notch 210 of outer trocar 208, as is approximately shown in FIG. 22. The exposed notches are again manipulated by pulling the whole assembly 180 proximally or pushing the whole assembly distally until either edge portion 211 of notch 210 or exposed edge portion 183 of notch 182 catches another piece of the pleura, after which inner cutting cannula 204 may be pushed inwardly relative to outer trocar to sever a piece of the pleura between edge portions 183 and 211 as is shown in FIG. 23. Thus, two samples will have been collected in a single procedure.

A fourth embodiment of the present invention is shown in FIGS. 24-26. The device is for thoracentesis, and is similar to needle assembly 160. Major differences between two devices are in the structure and shape of the tips of needle components.

The fourth embodiment comprises a needle assembly generally indicated at 186 as being comprised of two parts, inner needle portion 188 and outer needle portion 190. The inner portion 188 is comprised of an inner cannula 192 that is directly connected to plunger 191 by any suitable method such as those previously discussed. Cannula 192 is hollow and its lumen extends from a tapered tip 193 to aperture 178 positioned slightly distally of rubber gasket 134 on plunger 191.

The outer portion 190 is comprised of a syringe barrel 108, a T-shaped connector 119, a needle support 172 and a hollow outer trocar 194 having a tapered tip 195. Unlike needle assembly 160, each of distal ends of both inner needle 192 and outer needle 194 do not have notches but rather have solid side walls. To use assembly 186, it is inserted into the desired location from where fluid needs to be drained. By pumping motion of plunger 198 relative to barrel 108, or by connecting a suitable suction device to outlet 120 of connector 119, following removal of cap 122, fluid may be pumped or continuously withdrawn through outlet 120.

During a pleural biopsy procedure, direction of notches 114 or 168 (for cutting sample pleura) at the tip of needles should preferably be inferior but this is not a requirement. Nonetheless, to ensure the correct position of the notches one to the other, or the position of the inner cutting cannula to the outer trocar, each of the outer trocars with distal notches are attached to barrel 108 of a syringe such that a particular point on the syringe handle 196 is in the same direction as the notch. This alignment could also be keyed to the outlet 120, or to some other definable or identifiable point, location or structure.

Figure 27:
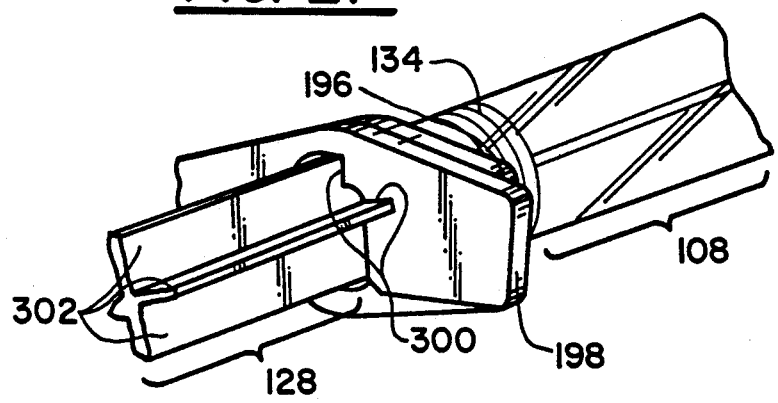
FIG. 27 shows an end perspective view of a portion of a syringe barrel, plunger and a plunger guide.

Notch 182 is desirably also kept in inferior orientation during a pleural biopsy procedure but what is essential is its position relative to notch 210. Since plunger 128 is free to rotate about its longitudinal axis, the orientation of notch 182 may rotate relative to trocar 208 and notch 210 and not be fully exposable to within notch 210. To prevent such rotation of plunger 128, a plunger guide 198 as shown in FIG. 27, may be used with the syringe. Plunger guide 198 may be fit over onto handle section 196, and includes a plurality of slots 300 for slidably receiving ribs 302 of plunger 128. Using plunger guide 198 with the syringe can ensure that notch 182 will be kept in the desired relationship or orientation with notch 210 throughout the pleural biopsy procedure. Slots 304 in plunger 191, shown in FIG. 25, are provided to allow plunger 191 to be rotated with slots 304 fitting over the thickness of guide 198. Rotation through 90° is possible until a solid rib in plunger 191 hits guide 198 at one of the edges forming slots 300 in guide 198.

For other embodiments, it still may be desirable to keep inner needles at a particular orientation relative to the outer needles during pleural biopsy or thoracentesis. For example, when using needle assembly 100, it may be desirable to have hollow trocar 126 rotatably oriented relative to trocar 110 so that the distal point of the tapered tip 130 is oriented to be approximately aligned with the hook 112 of notch 114. Again, in such cases, plunger guide 198 may be used with the syringe and plunger assembly.

Traditionally, during pleural biopsy procedures using conventional Abram's needle or Cope needle, the replacement of inner needles always temporarily exposed the patient's pleural cavity 154 to external air, endangering the patient to pneumothorax.

In each of the various embodiments of the present invention, as mentioned previously, the pleural cavity 154 of a patient, the lumen of innermost cannula, and the syringe cavity 142 collectively form a closed, connected space with aspirated pleural fluid acting to prevent airflow therethrough. If cap 122 is removed, external or atmospheric air or fluid is prevented from entering that connected space and the syringe by the normally closed flap valve 144; thus, the connected space is virtually enclosed by the inner surface of needles, the patient's chest walls, and the syringe at all times. As a consequence, the pleural cavity of a patient is not exposed to external or atmospheric air during any phase of the pleural biopsy procedure. Thus, with the present invention, the external air cannot enter the pleural cavity 154 and the danger of occurrence of pneumothorax is greatly reduced. Further, the biopsy procedure is simplified by the present invention which eliminates the need for the total withdrawal of removal of any portion of the once assembled structure during the procedure. One combined assembly is, in each embodiment, used throughout the procedure.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A biopsy device comprising, in combination, a syringe barrel having fixed thereto a first elongated, hollow needle having a sharpened distal end and a first inner diameter, said first needle including means defining a first elongated opening in a side wall thereof leading into the lumen and extending along a predetermined axial length thereof for a distance greater than the diameter of the needle and for a predetermined partial circumferential extent thereabout, said first elongated opening including at least one tissue engaging edge, said first elongated opening being spaced axially toward a proximal end from the sharpened distal end, said first needle further including means defining an aperture extending through the side wall opposite from said first elongated opening and a syringe plunger, operative within said syringe barrel, having fixed thereto a second elongated, hollow needle having a distal end and an outer diameter that is smaller than said first inner diameter, said second needle being slidingly received within said first needle, said second needle having means defining an aperture leading into the lumen of said second needle, said aperture being positioned adjacent the distal end of said plunger, and further including means defining a second elongated opening in a side wall thereof leading into the lumen an extending along the axial length thereof for a distance greater than the diameter of the second needle and for a predetermined circumferential extent thereabout to form a tissue engaging edge, said second elongated opening being spaced proximally a predetermined distance from said distal end.

2. A biopsy device as in claim 1 wherein said first needle further includes a sharpened distal end.

3. A biopsy device as in claim 1 further including a connector member positioned between said first needle and said syringe barrel.

4. A biopsy device as in claim 1 wherein said second needle has a sharpened distal end.

5. A biopsy device as in claim 1 wherein the opening in each of said first and second needles includes at least one sharp edge.

6. A biopsy device as in claim 1 further including a connector member positioned between said first needle and said syringe barrel, said connector member including a normally closed outlet.

7. A biopsy device as in claim 6 wherein said normally closed outlet includes a removable cap.

8. A biopsy device as in claim 6 wherein said normally closed outlet includes a pressure activated flap valve.

9. A biopsy device as in claim 8 wherein a positive pressure activates said flap valve into an open position.

10. A biopsy device as in claim 9 further including means for respectively locating and aligning said first and second needles.

11. A biopsy device as in claim 9 further including means for respectively locating and aligning the openings in said first and second needles.

* * * * *